United States Patent [19]

Blickenstaff, deceased et al.

[11] Patent Number: Plant 5,583

[45] Date of Patent: Dec. 3, 1985

[54] ALMOND TREE ("WOOD COLONY")

[76] Inventors: David E. Blickenstaff, deceased, late of Modesto, Calif.; by Esther L. Blickenstaff, Trustee, 617 W. Granger - No. 33, Modesto, Calif. 95350

[21] Appl. No.: 593,496

[22] Filed: Mar. 26, 1984

[51] Int. Cl.[4] ..... A01H 5/00

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is of medium size, medium vigor, open, and spreading; foliated in medium quantity with medium size, lanceolate, abruptly pointed leaves having a finely serrate margin and globose glands; blooms late and heavily with white flowers; and is a regular and productive bearer of a heavy, well-set, late-harvesting crop of medium size nuts having a relatively large, elongated, flat, sweet kernel of good quality.

1 Drawing Figure

BACKGROUND OF THE VARIETY

1. Field of the Invention

During his lifetime, inventor David Elmer Blickenstaff, now deceased, did, as an orchardist, frequent his ranch—located in Stanislaus County, Calif.—attendant the operation of the premises, including soil preparation for planting, cultivation, irrigation, and—in particular—inspection and maintenance of an almond orchard on such premises. Against such background of inventor's activities, the present variety of almond tree was discovered.

2. Classification of the Variety

The present new and distinct variety of almond tree is embraced by Class 30, Plants, of the United States Patent Office Manual of Classifiation.

PRIOR VARIETIES

Among the prior varieties of almond trees which were known to inventor, particular reference is made to Nonpareil and Ne Plus (both unpatented), and Carmel (U.S. Plant Pat. No. 2,641).

ORIGIN OF THE VARIETY

The present variety of almond tree was discovered, by inventor, in his orchard located as aforesaid, growing as a tree characteristically distinct from the Nonpareil and Carmel almond trees in such orchard. Subsequent to inventor's discovery of such untypical almond tree, he maintained the tree under continuing and careful observation, taking particular note of the distinct characteristics thereof, and which appeared to be of significant advantage in an almond tree for commercial growing.

ASEXUAL REPRODUCTION OF THE VARIETY

A number of the present variety of almond tree were asexually reproduced—on inventor's behalf by a commercial nursery—by budding, and, in maturity, such reproductions ran true to the original tree in all respects.

SUMMARY OF THE VARIETY

The present variety of almond tree is, characteristically, of medium size, medium vigor, open, and spreading; foliated in medium quantity with medium size, lanceolate, abruptly pointed leaves having a finely serrate margin and globose glands; blooms late and heavily with white flowers; and is a regular and productive bearer of a heavy, well-set, late-harvesting crop of medium size nuts having a relatively large, elongated, flat, sweet kernel of good quality.

The present variety of almond tree is further, and more particularly, characterized in the following respects:

The tree develops a very sturdy scaffold structure with many nut-bearing limbs and spur growth disposed radially around the scaffolded limbs; the tree—which is slightly smaller than the average commercial almond tree—having minimal sucker growth interior of the tree. By virtue of the smaller size of the tree and its very sturdy scaffold structure, the tree—especially with good initial pruning practice—has limbs which consistently and effectively support the heavy crop without the limbs breaking or hanging too low prior to harvest. The tree is relatively slow growing and, after initial selective pruning of the young tree, only slight pruning is necessary; the tree, in maturity, inherently tending to maintain the desirable scaffolding structure.

The tree blooms two to three days after the Nonpareil and is an excellent pollinizer for both the Nonpareil and Carmel; the tree thus being well adapted for interplanting either in "windrow" or "diamond" type orchard plantings.

The tree—which initially produces a harvestable crop in the fourth leaf—bears nuts which both knock and hull easily; the nuts—while pre-dropping few at the stage of dehiscence—breaking in a large part from the hull during knocking while the remainder are readily hulled by conventional methods and equipment. The nuts, both as to shell and kernel size, are similar to the Ne Plus, and the shell is relatively soft and similar to the Carmel. The harvest period of the nuts is late as compared to the Nonpareil.

BRIEF DESCRIPTION OF THE DRAWING

The drawing is an illustration, by photographic reproduction, in color, of a twig with leaves and a cluster of nuts; detached, in-hull nuts; detached out-of-hull nuts; and separate kernels.

DESCRIPTION OF THE VARIETY

The botanical details of this new and distinct variety of almond tree—with color definitions (except those in common color terms) referenced to Maerz and Paul Dictionary of Color (First Edition)—are as follows:

Tree:
- *Size.*—Medium.
- *Density.*—Open.
- *Vigor.*—Medium.

Trunk:
- *Size.*—Stocky.
- *Texture.*—Shaggy.

Branches:
- *Size.*—Stocky.
- *Texture.*—Medium.
- *Lenticels.*—Few. Large.
- *Branching habit.*—Spreading.
- *Color.*—New wood — Brown. Dull. Mature wood — Brown. Dull.

Foliage:
- *Quantity.*—Medium.

Leaves:
- *Size.*—Medium. Average length — 100.3 mm. Average width — 20.9 mm.
- *Shape.*—Lanceolate. Abruptly pointed.
- *Thickness.*—Thin.
- *Texture.*—Smooth.
- *Margin.*—Finely serrate.
- *Petiole.*—Medium length. Medium thickness.
- *Glands.*—Average number — 2. Alternate. Small. Globose. Green. Distal on petiole, and on blade.
- *Stipules.*—Wanting.
- *Color.*—Top side — Medium dark green (22-L-7). Under side — Dull lighter green (22-J-6).

Bloom:
- *Amount of bloom.*—Heavy.
- *Color.*—White.
- *Blooming period.*—February 15th - February 18th. Late, as compared with Nonpareil.

Crop:
- *Bearing.*—Regular bearer.
- *Productivity.*—Heavy.
- *Distribution of nuts on tree.*—Well distributed.
- *Harvest period.*—September 10th - September 13th. Late, as compared to Nonpareil.
- *Tenacity.*—Hangs well on tree. Easy to harvest. Easy to hull.

Hull:
- *Outer surface.*—Rough.
- *Pits.*—Pitted.
- *Form.*—Regular.
- *Thickness.*—Thin.
- *Flesh.*—Tough.
- *Suture.*—Flat depressed.
- *Color.*—Light green (21-J-5) with silvery sheen.
- *Dehiscence.*—Opens freely.

- *Splitting.*—Along suture.

Nut:
- *Size.*—Medium. Average length — 37.6 mm. Average width — 21.4 mm. Average thickness — 14.8 mm. Average weight — 2.55 grams.
- *Form.*—Length/Width — Elongated. Width/-Thickness — Medium.
- *Shell.*—Soft. Thin. Smooth. Outer shell — Hard. Inner shell — Hard. Well sealed.
- *Color.*—Medium light brown (12-J-6).
- *Pits.*—Large. Few. Deep. Round.
- *Base.*—Ventrally oblique.
- *Stem scar.*—Large. Obtuse.
- *Apex.*—Obtuse. Sharp. Blunt. Tip recurved.
- *Wing.*—Narrow. Thin. Tapered toward base.
- *Inner surface.*—Dark colored.
- *Ventral streak.*—Dark. Narrow.
- *Percentage of kernel to nut.*—61.1%.

Kernel:
- *Size (compared to Nonpareil).*—Large. Average length — 27.47 mm. Average width — 13.77 mm. Average thickness — 8.87 mm. Average weight — 0.55 ounce.
- *Form.*—Length/Width Elongated. Width/Thickness Flat.
- *Base.*—Ventrally oblique.
- *Stem scar.*—Large. Obtuse.
- *Apex.*—Obtuse. Sharp. Shouldered. Tip recurved.
- *Texture.*—Wrinkled. Furrowed.
- *Pellicle.*—Thick.
- *Pubescence.*—Veined.
- *Color.*—Light brown (13-L-9).
- *Number of doubles.*—Medium.
- *Flavor.*—Sweet.
- *Quality.*—Good.

RESISTANCE TO INSECTS AND DISEASES

Comparable to Carmel.

The almond tree and its nuts herein described may vary in slight detail due to climatic and soil conditions under which the variety may be grown; the present description being of the variety as grown in the Central Valley of California.

It is claimed:

1. A new and distinct variety of almond tree, substantially as illustrated and described, particularly characterized by relatively small size and slow growth, by a sturdy scaffold structure with many nut-bearing limbs and spur growth about the scaffold limbs, by minimal sucker growth interior of the tree, by blooming and harvesting after the Nonpareil, by excellent pollinization of other varieties such as the Nonpareil and Carmel, by bearing nuts which have minimal pre-drop at dehiscence but easily harvest and hull, most nuts breaking from the hull at harvest, and the nuts both as to the shell and kernel size being similar to the Ne Plus, and the shell being relatively soft and similar to the Carmel.

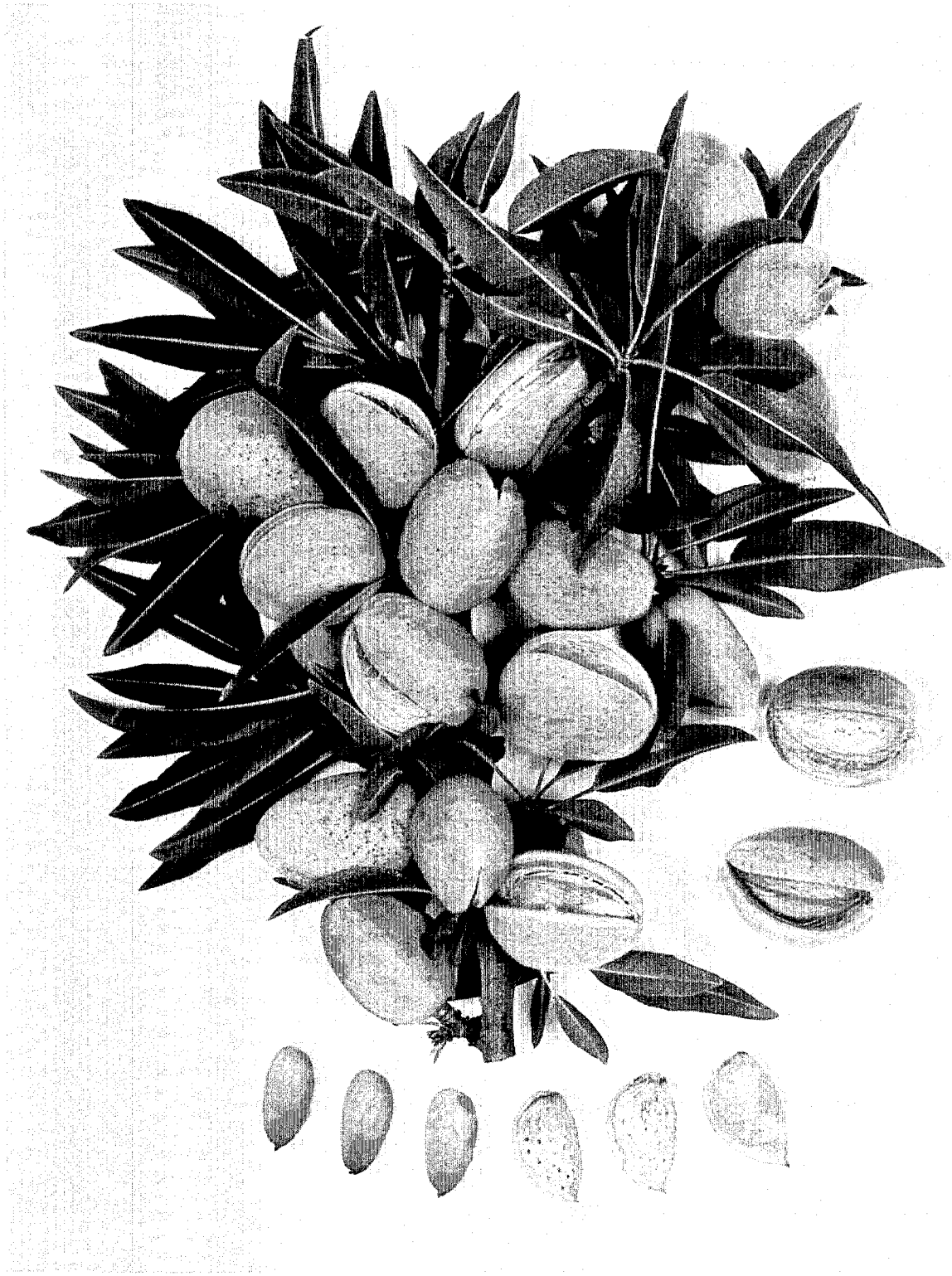

* * * * *